United States Patent
Hell et al.

(10) Patent No.: US 9,551,658 B2
(45) Date of Patent: Jan. 24, 2017

(54) STED MICROSCOPY WITH PULSED EXCITATION, CONTINUOUS STIMULATION, AND GATED REGISTRATION OF SPONTANEOUSLY EMITTED FLUORESCENCE LIGHT

(71) Applicants: Max-Planck-Gesellschaft zur Foerderung der Wissenschaften e.V., Munich (DE); Deutsches Krebsforschungszentrum, Heidelberg (DE)

(72) Inventors: Stefan W. Hell, Goettingen (DE); Johann Engelhardt, Bad Schoenborn (DE); Matthias Reuss, Sundbyberg (SE); Volker Westphal, Hannover (DE); Christian Eggeling, Goettingen (DE); Gael Moneron, Paris (FR); Kyu-Young Han, Urbana, IL (US); Giuseppe Vicidomini, Genoa (IT); Katrin Willig, Goettingen (DE)

(73) Assignees: MAX-PLANCK-GESELLSCHAFT ZUR FOERDERUNG DER WISSENSCHAFTEN E.V., Munich (DE); DEUTSCHES KREBSFORSCHUNGSZENTRUM, Heidelberg (DE)

(*) Notice: Subject to any disclaimer, the term of this patent is extended or adjusted under 35 U.S.C. 154(b) by 592 days.

(21) Appl. No.: 13/899,938

(22) Filed: May 22, 2013

(65) Prior Publication Data

US 2013/0256564 A1 Oct. 3, 2013

Related U.S. Application Data

(63) Continuation-in-part of application No. PCT/EP2010/067956, filed on Nov. 22, 2010.

(51) Int. Cl.
*F21V 9/16* (2006.01)
*G01N 21/64* (2006.01)
(Continued)

(52) U.S. Cl.
CPC ............ G01N 21/64 (2013.01); G01N 21/636 (2013.01); G01N 21/6408 (2013.01);
(Continued)

(58) Field of Classification Search
CPC ............ G01N 21/6454; G01N 21/6458; G01N 21/6456
See application file for complete search history.

(56) References Cited

U.S. PATENT DOCUMENTS 6,184,535 B1 2/2001 Kashima et al.
6,262,423 B1 * 7/2001 Hell et al. .................. 250/458.1
(Continued)

FOREIGN PATENT DOCUMENTS

| JP | 11-095120 | 4/1999 |
| JP | 2000-241782 | 9/2000 |
| WO | 2009/024529 A1 | 2/2009 |

OTHER PUBLICATIONS

Auksorius et al. "Stimulated emission depletion microscopy with supercontinuum source and fluorescence lifetime imaging" Physics Department, Imperial College London, Jan. 15, 2008/ vol. 33, No. 2/ Optics Letters p. 113-115.*
(Continued)

*Primary Examiner* — David Porta
*Assistant Examiner* — Mamadou Faye
(74) *Attorney, Agent, or Firm* — Thomas | Horstemeyer, LLP

(57) ABSTRACT

In a STED fluorescence light microscope pulses of excitation light (3) are applied to a sample, which excite fluorescent entities contained in the sample for fluorescence, and
(Continued)

which are focused on at least one focal area. Further, de-excitation light (12) is applied to the sample, which de-excites the excited fluorescent entities and which comprises an intensity zero point in the at least one focal area, as a continuous wave. Fluorescence light emitted by the excited fluorescent entities in the sample is registered after each pulse of the excitation light (3) and overlapping with applying the de-excitation light (13) with high temporal resolution between consecutive pulses of the excitation light (3).

45 Claims, 3 Drawing Sheets

(51) Int. Cl.
    *G01N 21/63*     (2006.01)
    *G02B 21/00*     (2006.01)
    *G02B 21/16*     (2006.01)

(52) U.S. Cl.
    CPC ..... *G01N 21/6458* (2013.01); *G02B 21/0076* (2013.01); *G02B 21/16* (2013.01)

(56) References Cited

U.S. PATENT DOCUMENTS

| | | | |
|---|---|---|---|
| 2001/0045529 A1* | 11/2001 | Iketaki et al. | 250/493.1 |
| 2004/0073119 A1* | 4/2004 | Mycek et al. | 600/476 |
| 2007/0025662 A1* | 2/2007 | Gugel | 385/39 |
| 2007/0057211 A1* | 3/2007 | Bahlman et al. | 250/584 |
| 2010/0176307 A1* | 7/2010 | Hell et al. | 250/459.1 |
| 2010/0213389 A1* | 8/2010 | Larkin et al. | 250/459.1 |
| 2011/0217694 A1* | 9/2011 | Buzatu et al. | 435/5 |

OTHER PUBLICATIONS

Moneron et al. "Two-photon excitation STED microscopy" Department of NanoBiophotonics, Max Planck Institute for Biophysical Chemistry, Aug. 17, 2009/ vol. 17, No. 17/ Optics Express p. 14567-14573.*

Auksorius, Egidijus et al.: "Stimulated emission depletion microscopy with a supercontinuum source and fluorescence lifetime imaging" (Optics Letters, vol. 33, No. 2, 2008).

Gael Moneron, et al., "Two-Photon Excitation STED Microscopy", Optics Express, vol. 17, No. 17, Aug. 3, 2009, pp. 14567-14573.

Kuang Cuifang, et al., "Far-Field Optical Nanoscopy Based on Contin9ous Wave Laser Stimulated Emission Depletion", Review of Scientific Instruments, AIP, Melville, NY, US, vol. 81, No. 5, May 28, 2010, p. 53709.

Gael Moneron, et al., "Fast STED Microscopy with Continuous Wave Fiber Lasers", Optics Express, vol. 18, No. 2, Jan. 12, 2010, pp. 1302-1309.

Jeffrey R. Moffitt, et al., "Time-Gating Improves the Spatial Resolution of STED Microscopy", Optics Express, vol. 19, No. 5, Feb. 28, 2011, pp. 4242-4254.

Kyu Young Han, et al., "Photoswitching of Color centers in Diamond and Its Applications to Far-Field Optical Nanoscopy", Seoul National University, Department of Chemistry, 2002.

PCT Search Report and Written Opinion in co-pending related PCT Application No. PCT/EP2010/067956, mailed Jul. 27, 2011.

* cited by examiner

STED MICROSCOPY WITH PULSED EXCITATION, CONTINUOUS STIMULATION, AND GATED REGISTRATION OF SPONTANEOUSLY EMITTED FLUORESCENCE LIGHT

CROSS-REFERENCE TO RELATED APPLICATION

This application is a continuation-in-part of copending PCT Application No. PCT/EP2010/067956, filed Nov. 22, 2010, entitled, "STED Microscopy with Pulsed Excitation, Continuous Stimulation, and Gated Registration of Spontaneously Emitted Fluorescence Light."

FIELD OF THE INVENTION

The present invention generally relates to a STED fluorescence light microscopic method and to a STED fluorescence light microscope suitable for executing this method. Particularly, the STED fluorescence light microscopic method may be executed for imaging a structure which is marked with fluorescent entities in a sample, or as a fluorescence correlation spectroscopic (FCS) method of observing fluctuations of fluorescent entities contained in a sample within a spatially limited volume of the sample.

The fluorescent molecules may particularly be fluorescent molecules or fluorescent quantum dots.

BACKGROUND OF THE INVENTION

Stimulated emission depletion (STED) fluorescence light microscopy allows for a spatial resolution in imaging a structure which is marked with fluorescent entities in a sample, or in delimiting the observation volume in FCS, which surpasses the diffraction barrier. This is achieved in that, after exciting the fluorescent entities for fluorescence by the excitation light, the spatial distribution of the excited fluorescent entities is altered by de-excitation or STED light stimulating the excited fluorescent entities for stimulated emission. Whereas the excitation light may only be focussed to a focal area with spatial dimensions above the diffraction barrier, a zero point of the intensity of the de-excitation light in which the excited fluorescent entities are not kept dark in that they are returned to their ground state by stimulated emission and are thus still able to emit fluorescence light, and around which the fluorescent entities are completely de-excited again, may be made much smaller. For example, the zero point of the intensity distribution of the de-excitation light may be defined by destructive interference of different components of the de-excitation light; and with increasing overall intensity of the de-excitation light the boundary of such a zero point beyond which the fluorescent entities are completely de-excited is closely drawn around a geometric point.

In STED fluorescence light microscopy, the excitation light is usually applied to the sample in pulses. Typically, the de-excitation light is also applied to the sample in pulses, and a detector for registering the fluorescence light emitted out of the zero point of the intensity distribution of the de-excitation light is only turned on directly after each pulse of the de-excitation light fades out.

As already indicated above, however, the de-excitation light needs to have a rather high intensity to yield a high spatial resolution. Pulsed lasers delivering high intensity pulses are expensive, particularly, if the pulses have to be very short, i.e. shorter than the lifetime of the excited state of the fluorescent entities, during which the excited state already decays by spontaneous emission of fluorescence light, as otherwise there would be no excited fluorescent entities left after each pulse of the de-excitation light, even in the zero point of its intensity distribution.

Besides applying both the excitation light and the de-excitation light in pulses as explained above, U.S. Pat. No. 5,731,588 also discloses to use a continuous wave laser as an excitation light source to save cost. Even then, the detector registering the fluorescence light spontaneously emitted out of the zero point of the intensity distribution of the de-excitation light is only turned on directly after each pulse of the de-excitation light has passed the sample.

US 2010/0176307 A1 discloses STED fluorescence light microscopy with two-photon excitation in which excitation light is applied to a sample in pulses at such a wavelength that fluorescent entities in the sample are excited for the emission of fluorescence light in a multi-photon process. The de-excitation or STED light is applied to the sample as a continuous wave, and the fluorescence light spontaneously emitted by the excited fluorescent entities in the sample is continuously recorded over several pulses of the excitation light. Due to the multi-photon process used for exciting the fluorescent entities in the sample, the spatial distribution of the excited fluorescent entities is assumed to not extend far beyond the zero point of the intensity distribution of the de-excitation light. Thus, it becomes possible to considerably save cost in that the de-excitation light is applied to the sample by a continuous wave laser, and in that the fluorescence light spontaneously emitted by the sample is continuously registered. In registering the spontaneously emitted fluorescence light, the excitation light, the de-excitation light and the stimulated emission from the fluorescent entities are blocked by a suitable edge filter or narrow-band bandpass filter and/or by means of a polarization filter, if the excitation light and the de-excitation light are suitably polarized.

The signal yield in any fluorescence light microscopic method using multi-photon excitation, however, is only small, and suitable pulsed light sources for exciting fluorescent entities in a multi-photon process, which have a suitable output intensity, are expensive.

A method of STED fluorescence light microscopy called CW-STED has been published which differs from that one disclosed in US 2010/0176307 A1 in that the excitation light applied to the sample in pulses excites the fluorescent entities for fluorescence in a simple one-photon process.

Both the two-photon excitation method disclosed in US 2010/0176307 A1 and CW-STED have been found to lack something of the expected spatial resolution. In fact, the images of a known structure marked with fluorescent entities look somewhat blurred as compared to images of the same structure obtained by pulsed excitation light and pulsed de-excitation light and by registering the spontaneously emitted fluorescence light only after each pulse of the de-excitation light.

Thus, a need remains for STED fluorescence light microscopy using a low-cost continuous wave laser but nevertheless exhibiting an uncompromised spatial resolution.

SUMMARY OF THE INVENTION

In one aspect, the present invention relates to a STED fluorescence light microscopic method of imaging a structure which is marked with fluorescent entities in a sample. The method of this aspect comprises the steps of: applying pulses of excitation light to the sample, which excite the fluorescent entities for fluorescence, and which are focused on at least one focal area; applying de-excitation light to the sample, which de-excites the excited fluorescent entities and which comprises an intensity zero point in the at least one focal area, as a continuous wave; registering fluorescence light spontaneously emitted by the excited fluorescent entities in the sample after each pulse of excitation light and overlapping with applying the de-excitation light; and repeating the steps of applying and registering at different positions of the focal area of the excitation light and the intensity zero point of the de-excitation light. In the step of registering, the fluorescence light spontaneously emitted by the excited fluorescent entities is registered with temporal resolution between consecutive pulses of the excitation light.

In another aspect, the present invention relates to a STED fluorescence correlation spectroscopic method of observing fluctuations of fluorescent entities contained in a sample within a spatially limited volume of the sample. The method of this aspect comprises the steps of: applying pulses of excitation light to the sample, which excite the fluorescent entities for fluorescence, and which are focused on at least one focal area; applying de-excitation light to the sample, which de-excites the excited fluorescent entities and which comprises an intensity zero point in the at least one focal area, as a continuous wave; and registering fluorescence light spontaneously emitted by the excited fluorescent entities in the sample after each pulse of excitation light and overlapping with applying the de-excitation light. In the step of registering, the fluorescence light spontaneously emitted by the excited fluorescent entities is registered with temporal resolution between consecutive pulses of the excitation light. In STED fluorescence correlation spectroscopic according to the present invention the spatially limited volume of the sample may be held spatially fixed in the sample so that the fluctuations are caused by movements of fluorescent probes in the sample. Alternatively, the spatially limited volume of the sample may be moved in the sample or with regard to the sample so that the fluctuations are also caused by fluorescent probes which are spatially fixed in the sample.

In a further aspect, the present invention relates to STED fluorescence light microscope that comprises: a pulsed excitation light source applying pulses of excitation light to a sample, which excite fluorescent entities contained in the sample for fluorescence, and which are focused on at least one focal area; a continuous wave de-excitation light source applying de-excitation light to the sample, which de-excites the excited fluorescent entities and which comprises an intensity zero point in the at least one focal area; a detector registering fluorescence light spontaneously emitted by the excited fluorescent entities in the sample after each pulse of excitation light and overlapping with applying the de-excitation light. The detector registers the fluorescence light spontaneously emitted by the excited fluorescent entities with temporal resolution between consecutive pulses of the excitation light source.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
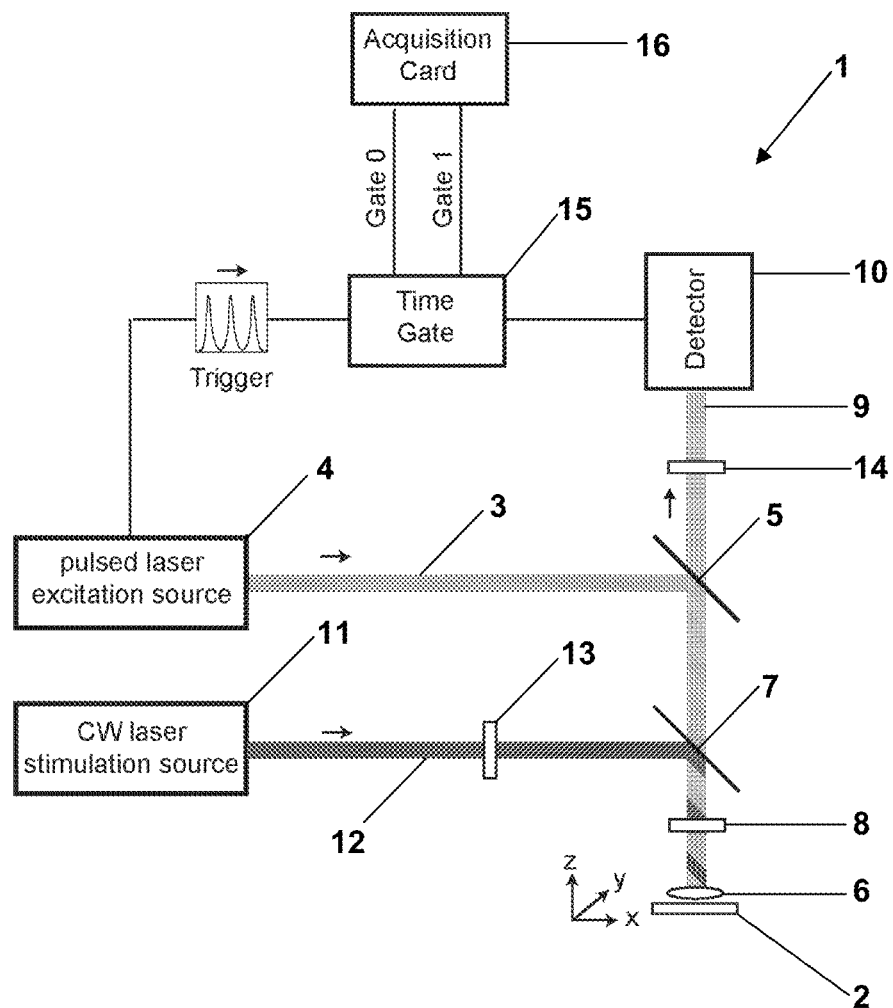
FIG. 1 shows the basic design of an embodiment of the new STED fluorescence light microscope.

Both in the new STED fluorescence light microscopic method of imaging a structure which is marked with fluorescent entities in a sample, and in the new STED-FCS method of observing fluctuations of fluorescent entities contained in a sample within a spatially limited volume of the sample, the fluorescence light emitted by the excited fluorescent entities is registered with high temporal resolution between consecutive pulses of the excitation light. I.e., even with a typical repetition rate of the pulses of the excitation light in the order of some ten MHz, the temporal resolution has to be considerably higher than the reciprocal value of this repetition rate. According to the present invention, the registration of the spontaneously emitted fluorescence light does not take place sometime between the pulses of the excitation light but during a defined interval in time in each period started with each pulse of the excitation light. This allows for discarding or not registering parts of the spontaneously emitted fluorescence light which come out of regions of the sample surrounding the zero point of the intensity distribution of the de-excitation light. The inventors of this invention found out that in fact these parts of the spontaneously emitted fluorescence light which exactly have the same optical properties as the parts of the fluorescence light emitted out of the zero point of the intensity distribution of the de-excitation light, are the reason why CW-STED images look blurred.

Despite discarding the fluorescence light spontaneously emitted out of other regions than the zero point of the intensity distribution of the de-excitation light, the high temporal resolution in registering the spontaneously emitted fluorescence light in the new methods allows for starting the registration of fluorescence light spontaneously emitted out of the zero point of the intensity distribution of the de-excitation light and thus for registering a maximum number of photons of the desired spontaneously emitted fluorescence light, directly after the fluorescent entities excited outside the zero point have been de-excited by the de-excitation light. During the entire registration of the spontaneously emitted fluorescence light, the de-excitation light is still applied as a continuous wave, and it is separated from the spontaneously emitted fluorescence light by a chromatic edge or band pass filter and/or by a polarization filter, if the de-excitation light is suitably polarized. These means also separate light emitted by the fluorescent entities due to stimulated emission from the spontaneously emitted fluorescence light to be registered. The high temporal resolution in registering the spontaneously emitted fluorescence light also allows for terminating the registration as soon as the signal to noise ratio starts to decrease with increasing distance in time to the last pulse of the excitation light and with a correspondingly decreasing remaining number of excited fluorescent entities in the zero point of the intensity distribution of the de-excitation light.

In STED-FCS the spatially limited observation volume is reduced to the zero point of the intensity distribution of the de-excitation light as the registered spontaneously emitted fluorescence light includes no contributions from entities outside the zero point.

In the new methods, the temporal resolution at which the fluorescence light emitted by the excited fluorescent entities is registered always has to be essentially higher than the lifetime of the excited state of the fluorescent entities, if the excited state decays by spontaneous emission of fluorescence light only.

Preferably, the temporal resolution is at least as high as the lifetime of the excited state of the fluorescent entities, if the excited state decays both by spontaneous emission of fluorescence light and by stimulated emission stimulated by the de-excitation light at its maximum intensity applied. This lifetime also defines the interval in time at which registering of the fluorescence light spontaneously emitted by the sample may be started after each pulse of the excitation light without registering fluorescence light spontaneously emitted by fluorescent entities outside the zero point of the intensity distribution of the de-excitation light. The absolute temporal resolution required for executing the new methods depends on the absolute values of the lifetimes indicated. Typically, the temporal resolution will be at least 200 ps. Preferably, the temporal resolution will be at least 100 ps.

An effective and non-expensive way of making use of the high temporal resolution in registering the spontaneously emitted fluorescence light is setting a time gate for the fluorescence light emitted after each pulse of the excitation light. The time gate may be implemented in a detector registering the spontaneously emitted fluorescence light in that the detector is only sensitive during the time gate. Alternatively, the gate may be used in separating the fluorescence light of particular interest from the overall fluorescence light registered by the detector. To this end, the time gate may be provided in addition to the detector itself. It has, however, to be noted that each device used in registering the fluorescence light has to have the high temporal resolution requested. Thus, a separate gate nevertheless requires a highly temporally resolving detector, i.e. a detector with very little time gitter. Suitable single photon counting detectors displaying a time gitter of not more than 100 ps are commercially available.

To the end of separating fluorescence light spontaneously emitted outside the zero point of the intensity distribution of the de-excitation light, the at least one gate is preferably opened after essentially all excited fluorescent entities outside the intensity zero point have emitted fluorescence light, either spontaneously or due to de-excitation by the de-excitation light.

The at least one gate is preferably closed prior to essentially all excited fluorescent entities in the focal area of the excitation light have emitted fluorescence light, as waiting for the fluorescence light emitted by the last remaining excited fluorescent entities will only decrease the signal to noise ratio.

Particularly with regard to the last paragraph, it has to be understood that any formulations like "prior to essentially all excited fluorescent entities in the focal area of the excitation light have emitted fluorescence light" have to be interpreted from a statistical point of view. After a particular pulse of the excitation light there may be no excited fluorescent entity at the intensity zero point of the de-excitation light at all, or the number of excited fluorescent entities at the zero point may only be very small, and they may all emit their fluorescence light very soon.

In the new methods, the at least one gate will preferably both be opened and closed at defined distances in time from each pulse of the excitation light. I.e. opening and closing the gate may be triggered by each pulse of the excitation light.

In the new methods, the at least one gate is not only opened but also be closed while still applying the de-excitation light as the de-excitation light is applied as a continuous wave. Applying the de-excitation light with a solid state cw laser, like for example a cw laser diode, allows for a considerable cost reduction in implementing the new methods.

It will be appreciated that each gate used in implementing the present invention is preferably adjustable with regard to both its opening and closing time such as to be able to fully adapt it to the fluorescent entities and the measurement conditions presently used. Further, the adjustability of the gate may be used for fine-tuning between a very narrow gate yielding a very high spatial resolution at very low light intensities only, and a wider gate yielding a lower spatial resolution but at much higher light intensities.

An embodiment of the new methods which is both particularly effective and cost-saving is having two complementary time gates which are alternately opened and closed. Such complementary gates are provided by commercially available devices which can be precisely triggered at very high frequencies.

The high temporal resolution in registering the spontaneously emitted fluorescence light may also be used to implement the new methods as two or multi color STED methods in that, for example, a first gate and a temporally consecutive second gate are set for the fluorescence light spontaneously emitted after each pulse of the excitation light, wherein the temporally consecutive gate is only opened after essentially all excited fluorescent entities of a first kind displaying a shorter lifetime than excited fluorescent entities of a second kind also contained in the sample have emitted their fluorescence light. As a result, only fluorescence light spontaneously emitted by excited fluorescent entities of the second kind are registered in the second time gate. Based on the intensity of the fluorescence light registered during the second gate, the concentration of the fluorescent entities of the second kind at the zero point of the intensity distribution of the de-excitation light can be determined. Considering this concentration, the fluorescence light intensity registered during the first gate may then be evaluated for the concentration of the fluorescent entities of the first kind at the zero point.

Instead of setting gates, the fluorescence light may also be registered in a plurality of temporally consecutive channels in the new methods. Then, the channels whose registered fluorescence light intensities or counts are evaluated may be selected later. There is no basic difference between setting a gate or selecting certain temporally consecutive channels for evaluation. However, implementing a gate with high temporal resolution may be implemented at lower cost than registering the fluorescence light in a plurality of temporally consecutive channels at the same temporal resolution.

In the new STED fluorescence light microscope, the detector registers the fluorescence light spontaneously emitted by the excited fluorescent entities with high temporal resolution between consecutive pulses of the excitation light source. The detector is preferably equipped with a time gate for separating the spontaneously emitted fluorescence light of interest. It is clear that the relevant temporal resolution in registering the spontaneously emitted fluorescence light is both determined by the detector itself and of any device with which the detector is equipped to only register the spontaneously emitted fluorescence light in a defined interval of time after each pulse of the excitation light from the excitation light source.

As already indicated, the detector may include a single photon counter providing the individual photon arrival times with very little time gitter, and a separate gate. Such a separate gate may be implemented electronically or in software. These two implementations are both known to those skilled in the art.

The new STED fluorescence light microscope may have a scanning stage for scanning the sample with the focal area of the excitation light source and the intensity zero point of the de-excitation light source. The scanning stage may either shift the sample or, which is preferred, use an optical element to simultaneously shift the focal area of the excitation light source, the intensity zero point of the de-excitation light source, and a detection area of the detector. The scanning stage is not necessary for using the new STED microscope in FCS.

Further details of the new STED microscope have already been explained when explaining the new methods of the invention.

It is clear that both the new methods and the new STED microscope may be used to apply the excitation light and the de-excitation light and to register the spontaneously emitted fluorescence light simultaneously with regard to several separate zero points of the intensity distribution of the de-excitation light within several separate focal areas of the excitation light. Other preferred embodiments of known STED microscopes may also be implemented together with the present invention. These embodiments include two-photon or multi-photon excitation of the fluorescent entities at the wavelength of the excitation light to enhance the spatial resolution in z-direction, and selecting the excitation light by its desired wavelength from a supercontinuum of wavelengths by an acousto-optical modulator, for example, to suit the absorption spectra of various fluorescent entities. Such a supercontinuum is typically produced by feeding high energy pulses from a laser into a suitable optical wave guide or fiber.

Referring now in greater detail to the drawings, FIG. 1 shows a STED fluorescence light microscope 1 according to the present invention. The microscope 1 may be used for FCS. The present embodiment, however, is destined for imaging a structure of interest in a sample 2 which is marked with fluorescent entities, and thus comprises a scanning stage indicated by arrows pointing in x-, y- and z-directions. The fluorescent entities in the sample 2 are excited for fluorescence by excitation light 3 emitted in pulses by an excitation light source 4. The excitation light 3 is reflected by a dichroic mirror 5 towards an objective 6 focusing the excitation light 3 in a focal area within the sample 2. Between the dichroic mirror 5 and the objective 6 the excitation light 3 passes through a further dichroic mirror 7 and through other optic elements 8. The focal area of the excitation light 3 focused by the objective 6 in the sample 2 has minimum dimensions limited by the diffraction barrier. I.e. fluorescence light 9 spontaneously emitted by the excited fluorescent entities in the sample and registered by a detector 10 may only be allocated to a certain point of the sample with a standard spatial resolution in optics. As a result, an image of the structure of interest in the sample 2 taken by scanning the sample 2 with the focused excitation light 3 only has a spatial resolution delimited by the diffraction barrier. To surpass the diffraction barrier, the STED microscope 1 comprises a further light source 11 providing STED or de-excitation light 12 as a continuous wave. By means of a phase mask 13 the wave fronts of the de-excitation light 12 are deformed in such a way that the intensity distribution of the de-excitation light 12 focused by the objective 6 exhibits a zero point within the focal area of the excitation light 3 in the sample 2. Everywhere outside this zero point the de-excitation light 12 stimulates the fluorescent entities excited by the excitation light 3 for stimulated emission. The stimulated light has the same wavelength as the de-excitation light 12 which differs from the wavelength of the spontaneously emitted fluorescence light 9 and may thus be blocked by a filter 14 arranged in front of the detector 10. Parts of the excitation light 3 and of the de-excitation light 12 reflected by the sample 2 are also blocked from the detector 10 by the filter 14. As a result, the detector 10 only registers fluorescence light spontaneously emitted out of the sample 2. The desired high spatial resolution in allocating the signal of the detector 10 to the zero point of the intensity distribution of the de-excitation light 12 is actually achieved here in that the detector displays a high temporal resolution in detecting the spontaneously emitted fluorescence light and in that a time gate 15 triggered by each pulse of excitation light 3 from the excitation light source 4 is used to separately collect the signals from the detector 10 in two gates 0 and 1 on an acquisition card 16.

Figure 2:
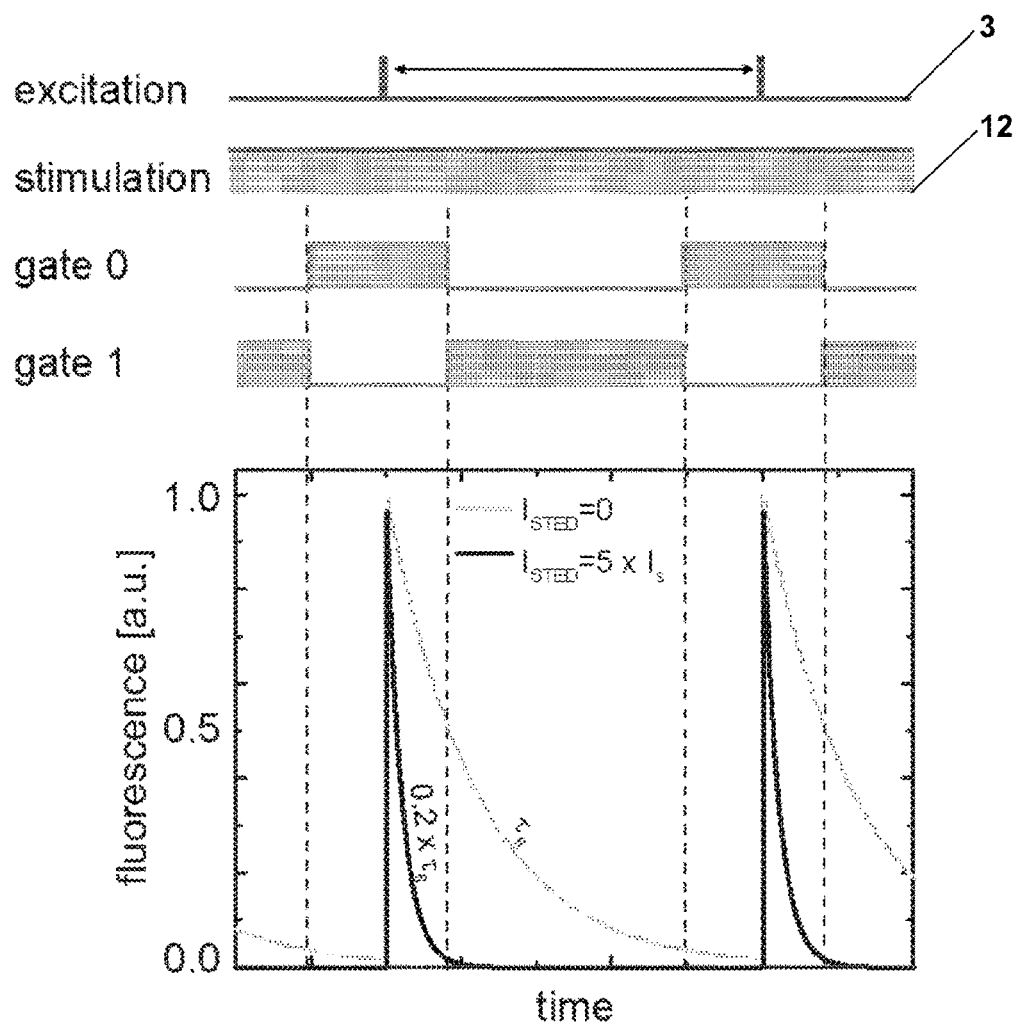
FIG. 2 depicts the time course of the excitation light, the time course of the de-excitation light, the opening times of two gates 0 and 1, and the intensity of the fluorescence light spontaneously emitted by an examined sample both in the zero point of intensity of the de-excitation light (gray line) and around this zero point (black line)

FIG. 2 indicates the time courses of the excitation light 3, the de-excitation light 12, the gates 0 and 1, and the fluorescence light intensity from the fluorescent entities in the sample. The fluorescence light intensity is both indicated for the zero point of the intensity distribution of the de-excitation light (gray line: $I_{STED}=0$), and for the surroundings of the zero point, where the intensity of the de-excitation light five-fold exceeds a saturation intensity $I_S$ at which a complete de-excitation of the excited fluorescent entities is achieved by stimulated emission within very short time. The time course of the fluorescence intensity in the zero point of the intensity distribution of the de-excitation light is defined by the lifetime of the excited state of the fluorescent entities only decaying by spontaneous emission of fluorescence light. In the surroundings of the zero point the time course of the fluorescence light intensity is defined by a lifetime strongly shortened as a result of the stimulated emission due to the de-excitation light.

The fluorescence light intensity registered with the detector 10 according to FIG. 1 both includes the spontaneously emitted fluorescence light from the zero point of the intensity distribution of the de-excitation light and out of its surroundings. By setting gate 1, however, in such a way that it only opens after the excited state of the fluorescent entities in the surroundings of the zero point has decayed and that is closes when essentially all fluorescent entities excited by the preceding excitation light pulse have emitted fluorescence light, the fluorescence light registered during gate 1 completely comes out of the zero point of the intensity distribution of the de-excitation light and may thus be allocated to this zero point. Gate 0 is complementary to gate 1. It closes when gate 1 opens, and it opens when gate 1 closes. The fluorescence light intensity registered in gate 0 both includes fluorescence light out of the zero point of the intensity distribution of the de-excitation light and out of its surroundings. Thus, the absolute intensity of the spontaneously emitted fluorescence light registered in gate 0 is considerably higher than the intensity registered in gate 1. Further, even in gate 0 the de-excitation light 12 strongly reduces the contribution by fluorescent entities outside the zero point of the intensity distribution of the de-excitation light. Thus, the spatial resolution is increased by the de-excitation light 12 beyond the diffraction barrier even if the fluorescence light intensity collected in gate 0 is evaluated only.

Figure 3:
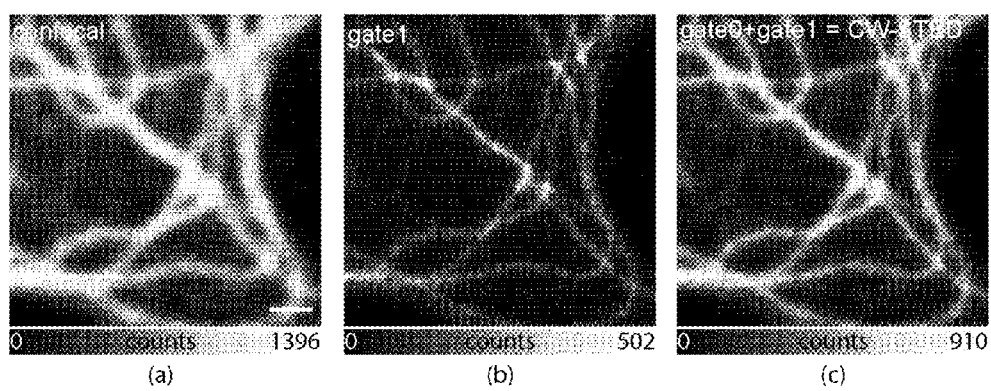
FIG. 3 shows three pictures taken of the same structure in a sample with the microscope according to FIG. 1. Picture (a) is taken in a simple confocal setup without using de-excitation light. Picture (b) is based on the fluorescence light intensity registered in gate 1 according to FIG. 2; and picture (c) is based on the sum of the fluorescence light intensity registered in gate 0 and gate 1 according to FIG. 2, which corresponds to a CW-STED setup.

FIG. 3 is a comparison of the spatial resolution achievable according to the present invention (b) with the spatial resolution achievable in confocal fluorescence light microscopy (a) and CW-STED microscopy (c). All images of FIG. 3 show the same structure in a sample marked with fluorescent entities. The brightest image (a) is that one acquired in the confocal mode in which the fluorescence light intensity is in no way reduced by de-excitation light. As a result, image (a) exhibits the lowest spatial resolution. Image (c) which has been acquired in CW-STED mode and which is obtainable by adding the intensities registered in gates 0 and 1 according to FIG. 2 already exhibits an increased spatial resolution at the cost of a reduced brightness. However, the structure still looks blurred. The image (b) acquired according to the present invention, i.e. based on the spontaneously emitted fluorescence light collected in gate 1 according to FIG. 2 only, exhibits a further increased spatial resolution at a further decreased brightness. However, the signal to noise ratio is still high so that the structure of interest is imaged with a high contrast against its surroundings.

The present invention allows for essentially reducing the intensity of the continuous wave of the de-excitation light. Due to setting the gate 1 for registering the relevant spontaneously emitted fluorescence light only, any signal registered in this gate can be directly allocated to the present position of the zero point of the intensity distribution of the de-excitation light in the sample. Lower light intensities are associated with lower damaging effects on the sample, particularly if it is a biological sample. Thus, the present invention also allows for examination of living biological samples without damaging them by applying very high light intensities. Particularly, the present invention may be implemented with as low as about 20 mW light power of the de-excitation light applied to in the focal area of the excitation light.

Many variations and modifications may be made to the preferred embodiments of the invention without departing substantially from the spirit and principles of the invention. All such modifications and variations are intended to be included herein within the scope of the present invention, as defined by the following claims.

LIST OF REFERENCE NUMERALS

1 microscope
2 sample
3 excitation light
4 excitation light source
5 dichroic mirror
6 objective
7 dichroic mirror
8 optics elements
9 spontaneously emitted fluorescence light
10 detector
11 de-excitation light source
12 de-excitation light
13 phase mask
14 filter
15 time gate
16 acquisition card

We claim:

1. A STED fluorescence light microscopic method of imaging a structure which is marked with fluorescent entities in a sample, the method comprising the steps of:
    applying pulses of excitation light to the sample, which excite the fluorescent entities for fluorescence, and which are focused on at least one focal area;
    applying de-excitation light to the sample, which de-excites the excited fluorescent entities and which comprises an intensity zero point in the at least one focal area, as a continuous wave;
    registering fluorescence light spontaneously emitted by the excited fluorescent entities in the sample after each pulse of excitation light and overlapping with applying the de-excitation light; and
    repeating the steps of applying and registering at different positions of the focal area of the excitation light and the intensity zero point of the de-excitation light;
    wherein, in the step of registering, the fluorescence light spontaneously emitted by the excited fluorescent entities is registered with temporal resolution between consecutive pulses of the excitation light.

2. The method of claim 1, wherein, in the step of registering, the fluorescence light emitted by the excited fluorescent entities is registered at a temporal resolution which is higher than a life time of the excited state of the fluorescent entities decaying by spontaneous emission of fluorescence light only.

3. The method of claim 2, wherein, in the step of registering, the fluorescence light emitted by the excited fluorescent entities is registered at a temporal resolution which is at least as high as a life time of the excited state of the fluorescent entities decaying both by spontaneous emission of fluorescence light and by de-excitation due to the de-excitation light at its maximum intensity applied.

4. The method of claim 2, wherein, in the step of registering, the fluorescence light emitted by the excited fluorescent entities is registered at a temporal resolution which is at least 200 ps.

5. The method of claim 4, wherein, in the step of registering, the fluorescence light emitted by the excited fluorescent entities is registered at a temporal resolution which is at least 100 ps.

6. The method of claim 1, wherein, in the step of registering, at least one time gate is set for the fluorescence light emitted after each pulse of the excitation light.

7. The method of claim 6, wherein the at least one gate is opened directly after essentially all excited fluorescent entities outside the intensity zero point of the de-excitation light have emitted fluorescence light.

8. The method of claim 6, wherein the at least one gate is closed prior to essentially all excited fluorescent entities in the focal area of the excitation light have emitted fluorescence light.

9. The method of claim 6, wherein the at least one gate is both opened and closed at defined distances in time from each pulse of the excitation light.

10. The method of claim 6, wherein the at least one gate and a complementary gate are alternately opened and closed.

11. The method of claim 6, wherein, in the step of registering, the at least one gate and a temporally consecutive gate are set for the fluorescence light spontaneously emitted after each pulse of the excitation light, the temporally consecutive gate only being opened after essentially all excited fluorescent entities of a first kind displaying a shorter life time than excited fluorescent entities of a second kind also contained in the sample have emitted fluorescence light.

12. The method of claim 1, wherein, in the step of registering, the fluorescence light is registered in a plurality of temporally consecutive channels.

13. The method of claim 1, wherein, in the step of applying pulses of excitation light, a wave length of the excitation light is selected such as to excite the fluorescent entities for fluorescence via a multi-photon process.

14. The method of claim 1, wherein, in the step of applying pulses of excitation light, a wavelength of the excitation light is selected from a supercontinuum of wavelengths.

15. A STED fluorescence correlation spectroscopic method of observing fluctuations of fluorescent entities contained in a sample within a spatially limited volume of the sample, the method comprising the steps of:
   applying pulses of excitation light to the sample, which excite the fluorescent entities for fluorescence, and which are focused on at least one focal area;
   applying de-excitation light to the sample, which de-excites the excited fluorescent entities and which comprises an intensity zero point in the at least one focal area as a continuous wave; and
   registering fluorescence light spontaneously emitted by the excited fluorescent entities in the sample after each pulse of excitation light and overlapping with applying the de-excitation light;
   wherein, in the step of registering, the fluorescence light spontaneously emitted by the excited fluorescent entities is registered with temporal resolution between consecutive pulses of the excitation light.

16. The method of claim 15, wherein the spatially limited volume of the sample is held spatially fixed in the sample.

17. The method of claim 15, wherein the spatially limited volume of the sample is moved in the sample.

18. The method of claim 15, wherein, in the step of registering, the fluorescence light emitted by the excited fluorescent entities is registered at a temporal resolution which is higher than a life time of the excited state of the fluorescent entities decaying by spontaneous emission of fluorescence light only.

19. The method of claim 18, wherein, in the step of registering, the fluorescence light emitted by the excited fluorescent entities is registered at a temporal resolution which is at least as high as a life time of the excited state of the fluorescent entities decaying both by spontaneous emission of fluorescence light and by de-excitation due to the de-excitation light at its maximum intensity applied.

20. The method of claim 18, wherein, in the step of registering, the fluorescence light emitted by the excited fluorescent entities is registered at a temporal resolution which is at least 200 ps.

21. The method of claim 20, wherein, in the step of registering, the fluorescence light emitted by the excited fluorescent entities is registered at a temporal resolution which is at least 100 ps.

22. The method of claim 15, wherein, in the step of registering, at least one time gate is set for the fluorescence light emitted after each pulse of the excitation light.

23. The method of claim 22, wherein the at least one gate is opened directly after essentially all excited fluorescent entities outside the intensity zero point of the de-excitation light have emitted fluorescence light.

24. The method of claim 22, wherein the at least one gate is closed prior to essentially all excited fluorescent entities in the focal area of the excitation light have emitted fluorescence light.

25. The method of claim 22, wherein the at least one gate is both opened and closed at defined distances in time from each pulse of the excitation light.

26. The method of claim 22, wherein the at least one gate and a complementary gate are alternately opened and closed.

27. The method of claim 22, wherein, in the step of registering, the at least one gate and a temporally consecutive gate are set for the fluorescence light spontaneously emitted after each pulse of the excitation light, the temporally consecutive gate only being opened after essentially all excited fluorescent entities of a first kind displaying a shorter life time than excited fluorescent entities of a second kind also contained in the sample have emitted fluorescence light.

28. The method of claim 15, wherein, in the step of registering, the fluorescence light is registered in a plurality of temporally consecutive channels.

29. The method of claim 15, wherein, in the step of applying pulses of excitation light, a wave length of the excitation light is selected such as to excite the fluorescent entities for fluorescence via a multi-photon process.

30. The method of claim 15, wherein, in the step of applying pulses of excitation light, a wavelength of the excitation light is selected from a supercontinuum of wavelengths.

31. A STED fluorescence light microscope comprising:
   a pulsed excitation light source applying pulses of excitation light to a sample, which excite fluorescent entities contained in the sample for fluorescence, and which are focused on at least one focal area;
   a continuous wave de-excitation light source applying de-excitation light to the sample, which de-excites the excited fluorescent entities and which comprises an intensity zero point in the at least one focal area;
   a detector registering fluorescence light spontaneously emitted by the excited fluorescent entities in the sample after each pulse of excitation light and overlapping with applying the de-excitation light;
   wherein the detector registers the fluorescence light spontaneously emitted by the excited fluorescent entities with temporal resolution between consecutive pulses of the excitation light source.

32. The microscope of claim 31, wherein the detector registers the fluorescence light emitted by the excited fluorescent entities at a temporal resolution which is at least 200 ps.

33. The microscope of claim 32, wherein the detector registers the fluorescence light emitted by the excited fluorescent entities at a temporal resolution which is at least 100 ps.

34. The microscope of claim 31, wherein a time gitter of the detector is not more than 200 ps.

35. The microscope of claim 34, wherein a time gitter of the detector is not more than 100 ps.

36. The microscope of claim 31, wherein the detector includes a single photon counter.

37. The microscope of claim 31, wherein the detector is equipped with at least one time gate.

38. The microscope of claim 37, wherein the at least one time gate is triggered by each pulse of the excitation light source.

39. The microscope of claim 38, wherein the at least one gate is both opened and closed at adjustable distances in time from each pulse of the excitation light source.

40. The microscope of claim 37, wherein the detector is further equipped with a complementary gate, the at least one gate and the complementary gate being alternately opened and closed.

41. The microscope of claim 31, wherein the de-excitation light source is a continuous wave laser diode.

42. The microscope of claim 31, wherein the pulsed excitation light source emits excitation light having a wavelength which is about twice as long as a wavelength of the fluorescence light registered by the detector.

43. The microscope of claim 31, wherein the pulsed excitation light source provides a supercontinuum of wavelengths from which a wavelength for the excitation light is selected by means of an acousto-optical modulator.

44. The microscope of claim 31, wherein the detector comprises a plurality of temporally consecutive channels.

45. The microscope of claim 31, further comprising a scanning stage for scanning the sample with the focal area of the excitation light from the excitation light source and the intensity zero point of the de-excitation light from the de-excitation light source.

\* \* \* \* \*